United States Patent [19]
Kitaoka et al.

[11] Patent Number: 5,662,637
[45] Date of Patent: Sep. 2, 1997

[54] DISPOSABLE ABSORBENT ARTICLE

[75] Inventors: Hideaki Kitaoka, Funabashi; Isamu Yamazaki, Tokyo; Makoto Suekane, Kawanoe, all of Japan

[73] Assignee: Uni-Charm Corporation, Ehime-ken, Japan

[21] Appl. No.: 351,190

[22] Filed: Nov. 30, 1994

[30] Foreign Application Priority Data

Dec. 2, 1993 [JP] Japan ................................. 5-302929

[51] Int. Cl.⁶ .................................................. A61F 13/15
[52] U.S. Cl. ...................... 604/385.2; 604/385.1; 604/393
[58] Field of Search ........................... 604/385.1, 385.2, 604/386, 393–398

[56] References Cited

U.S. PATENT DOCUMENTS

| | | | |
|---|---|---|---|
| 5,167,653 | 12/1992 | Igaue et al. | 604/385.2 |
| 5,304,160 | 4/1994 | Igaue et al. | 604/385.2 |
| 5,413,570 | 5/1995 | Enloe | 604/385.2 |

FOREIGN PATENT DOCUMENTS

| | | |
|---|---|---|
| 0433951 | 6/1991 | European Pat. Off. . |
| 0508477 | 10/1992 | European Pat. Off. . |
| 0532005 | 3/1993 | European Pat. Off. . |
| 0532034 | 3/1993 | European Pat. Off. . |
| 62-250201 | 10/1987 | Japan . |
| 2174845 | 7/1990 | Japan . |
| 3188851 | 8/1991 | Japan . |
| 3286760 | 12/1991 | Japan . |
| 4218157 | 8/1992 | Japan . |
| 499921 | 8/1992 | Japan . |
| 5042180 | 2/1993 | Japan . |
| 2216393 | 10/1989 | United Kingdom . |
| 2250921 | 6/1992 | United Kingdom . |
| WO 93/12746 | 7/1993 | WIPO . |

*Primary Examiner*—David Isabella
*Assistant Examiner*—K. M. Reichle
*Attorney, Agent, or Firm*—Lowe, Price, LaBlanc & Becker

[57] ABSTRACT

A disposable absorbent article such as a disposable diaper including first stretchable side flaps extending over transversely opposite outer zones of the diaper and second stretchable side flaps functioning as liquid-barriers each having a proximal edge and a distal edge arranged so as to define an exposed zone of a topsheet along each of transversely opposite side edge surfaces of a liquid-absorbent core and thereby, if a quantity of liquid excretions gets over the distal edge of the second side flaps, it can be absorbed by the liquid-absorbent core through the exposed zones.

2 Claims, 1 Drawing Sheet

DISPOSABLE ABSORBENT ARTICLE

BACKGROUND OF THE INVENTION

The present invention relates to disposable absorbent articles, particularly such as diapers or training pants, provided with stretchable side flaps in the form of double cuffs serving to form double seals around respective legs of the wearer, Japanese Laid-Open patent application No. 1987-250201 discloses a diaper as an example of the above-mentioned disposable absorbent article having double cuffs, Such a diaper includes first stretchable side flaps (gasket cuffs) extending outwards from transversely opposite edges of a liquid-absorbent core and second stretchable side flaps (barrier cuffs) provided on top surfaces of the respective first stretchable side flaps. The second side flaps each have a proximal edge and a distal edge. The side flaps are intended to eliminate the lateral flow and leakage of liquid excretions that might laterally flow out through the top surface of a topsheet overlying a top surface of said core. According to the disclosure, the second stretchable side flaps may be formed of either liquid-permeable or liquid-impermeable sheet. Consequently, types of the above mentioned excretions of which leakage must be avoided are considered to be semi-liquid or semi-solid excretions.

In such a diaper, the proximal edges of the respective second stretchable side flaps are bonded to the top surfaces of the respective first stretchable side flaps extending between the respective side edges of the liquid-absorbent core and the outer stretchable sealing zones of the respective first stretchable side flaps. With this arrangement, any quantity of liquid excretions leaking over the distal edges of the second stretchable side flaps will be trapped between the second stretchable side flaps and the sealing zones of the respective first stretchable side flaps but may finally leak outwardly of the sealing zones. While such outward leakage is serious particularly when the second stretchable side flaps are formed by liquid-impermeable sheets, it is impossible also for the second stretchable side flaps formed by liquid-permeable sheets to absorb the liquid excretions once trapped and thereby to prevent this from leaking outwardly of said sealing zones of the first stretchable side flaps, since no liquid-permeable sheets having a sufficient absorptivity for the liquid excretions are used to form the second stretchable side flaps.

Certainly, the relatively low absorptivity typically exhibited by the liquid-permeable sheets will be compensated by the relatively high absorptivity typically exhibited by the absorbent core as long as the second stretchable side flaps are formed by liquid-permeable sheets which are arranged in close contact with the liquid-permeable topsheet along the laterally opposite side edge surfaces of the liquid-absorbent core, since the liquid excretions will be then absorbed by the liquid-absorbent core through the respective second stretchable side flaps. However, the second stretchable side flaps do not have such an arrangement in the diaper according to the above-mentioned prior art.

Obviously, liquid excretions may often leak over the distal edges of the second stretchable side flaps and the first stretchable side flaps are provided for this reason.

It is a principal object of the invention to arrange the second stretchable side flaps so as to be able not only to dam semi-liquid or semi-solid excretions, but also to guide such excretions, if they leak over the distal edges of the second stretchable side flaps into the liquid-absorbent core through its laterally opposite side edges surfaces.

SUMMARY OF THE INVENTION

To achieve the object set forth above, the invention generally resides in a disposable absorbent article having a liquid-permeable topsheet, a liquid-impermeable backsheet, a liquid-absorbent core sandwiched between these two sheets, first stretchable side flaps comprising portions of the topsheet and backsheet extending outwards from transversely or laterally opposite side edges of the liquid-absorbent core and second stretchable side flaps disposed between positions adjacent the respective side edges of the liquid-absorbent core and respective outermost side edges of the first stretchable side flaps, the second side flaps each having proximal edges and distal edges with its longitudinally opposite ends fixed in a collapsed state. The invention is characterized in that the second stretchable side flaps which substantially function as liquid-barriers have proximal edges bonded to the top surface of the topsheet overlying the top surface of the liquid-absorbent core and the first stretchable side flaps have top surfaces covered with side sheets functioning as liquid-barriers so that the liquid-absorbent core may be liquid-permeable along its laterally opposite side edge surfaces.

Preferably, the portions of the topsheet extending outwards from the laterally opposite side edges of the liquid-absorbent core so as to constitute part of the respective first side flaps are narrower than the portions of the backsheet extending from the opposite side edges of the liquid-absorbent core so as to constitute part of the first stretchable side flaps and the outermost side edges of respective side sheets extend to the corresponding outermost side edges of the portions of the backsheet extending from the laterally opposite side edges of the liquid-absorbent core with no portion of the topsheet being interposed between the backsheet and the respective side sheets over the outer zones of the first stretchable side flaps.

Preferably, a cover sheet centrally provided with an opening extending in its longitudinal direction and functioning as a liquid-barrier covers the outer peripheral zone of the topsheet as well as longitudinally opposite ends of the respective second stretchable flaps. The outer peripheral zone of the cover sheet is bonded to the outer peripheral zone of the topsheet as well as to the longitudinally opposite ends of the respective second stretchable side flaps so that respective outer side zones of the cover sheet define the side sheets.

With the absorbent article according to the invention, if a quantity of liquid excretions leaks over the distal edges of the second stretchable side flaps, i.e., the quantity of liquid excretions having leaked out along paths defined between the distal edges and the wearer's skin, such quantity is trapped between the portions of the topsheet covering the liquid-absorbent core along its laterally opposite side edge surfaces and the respective sealing zones extending along the outer edges of the first stretchable side flaps around the wearer's legs. This quantity of liquid excretions is then at least partially guided into the liquid-absorbent core through its laterally opposite side edge surfaces under the relatively high absorptivity of the liquid-absorbent core. In this manner, such liquid excretions can be held by the liquid-absorbent core for a relatively long period, reducing the apprehension that the liquid excretions might directly contact the wearer's skin to give the wearer an unpleasant feeling and leak outwards from the first stretchable side flaps.

Certainly, the quantity of liquid excretions once absorbed by the liquid-absorbent core may soak out again through the side edge surfaces thereof since the topsheet is exposed and remains liquid-permeable along the side edge surfaces. However, the second stretchable side flaps are provided primarily to dam up semi-liquid or semi-solid excretions and a quantity of such excretions which have soaked out again through the side edge surfaces of the liquid-absorbent core, as has previously been described, can be at least partially absorbed again by the liquid-absorbent core through the side edge surfaces at which the soaking out has occurred. The disadvantage accompanying such arrangement of the invention is rather acceptable when compared to the previously mentioned disadvantage accompanying the arrangement of the prior art according to which the liquid excretions are trapped between the second stretchable side flaps and the sealing zones of the first stretchable side flaps and prevented from smoothly moving toward the liquid-absorbent core.

In view of its desired function, each second stretchable side flap must have its distal edge located at a predetermined height above the top surface of the topsheet overlying the top surface of the liquid-absorbent core and, according to the invention, this requirement is effectively met by bonding the proximal edge to the top surface of the topsheet overlying the top surface of the liquid-absorbent core. Such arrangement according to the invention allows the second stretchable side flap to be dimensioned lower (narrower) than in the arrangement having the proximal edge bonded to the associated first stretchable side flap. In this manner, the arrangement according to the invention allows the material cost to be reduced.

PREFERRED EMBODIMENTS OF THE INVENTION

Figure 1:
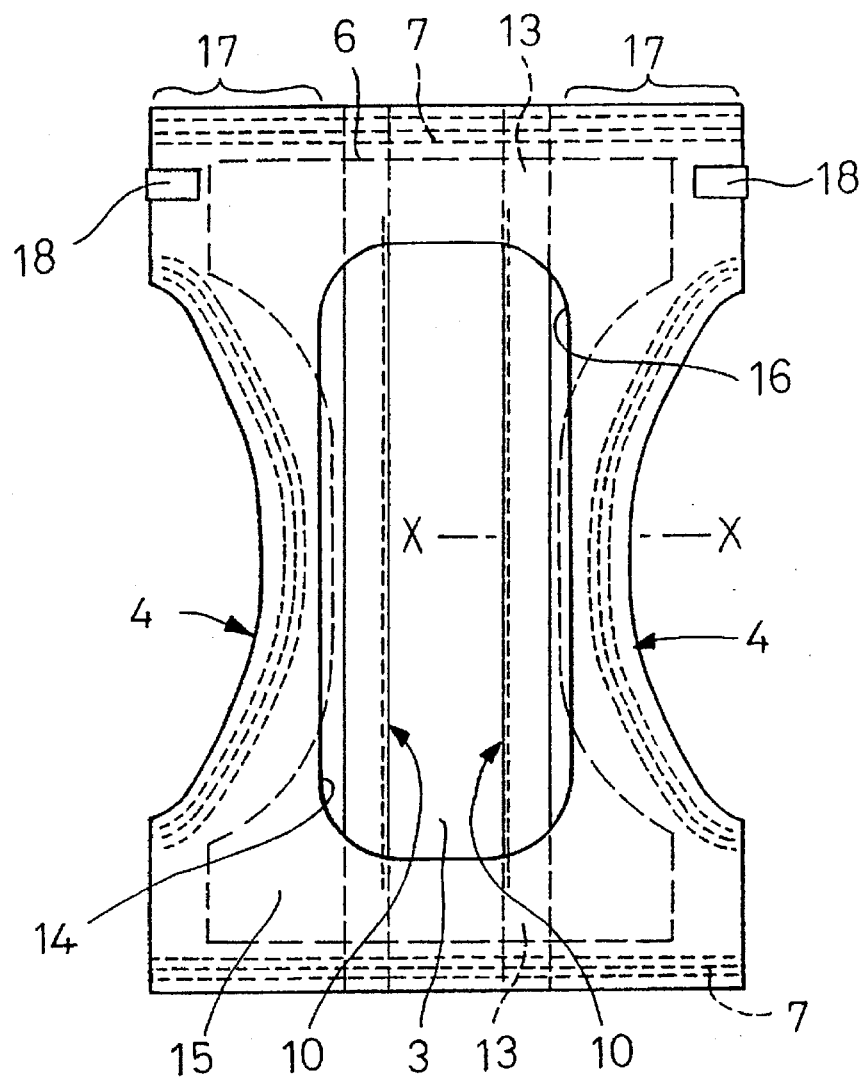
FIG. 1 is a plan view of a disposable diaper as an embodiment of the invention.
Figure 2:
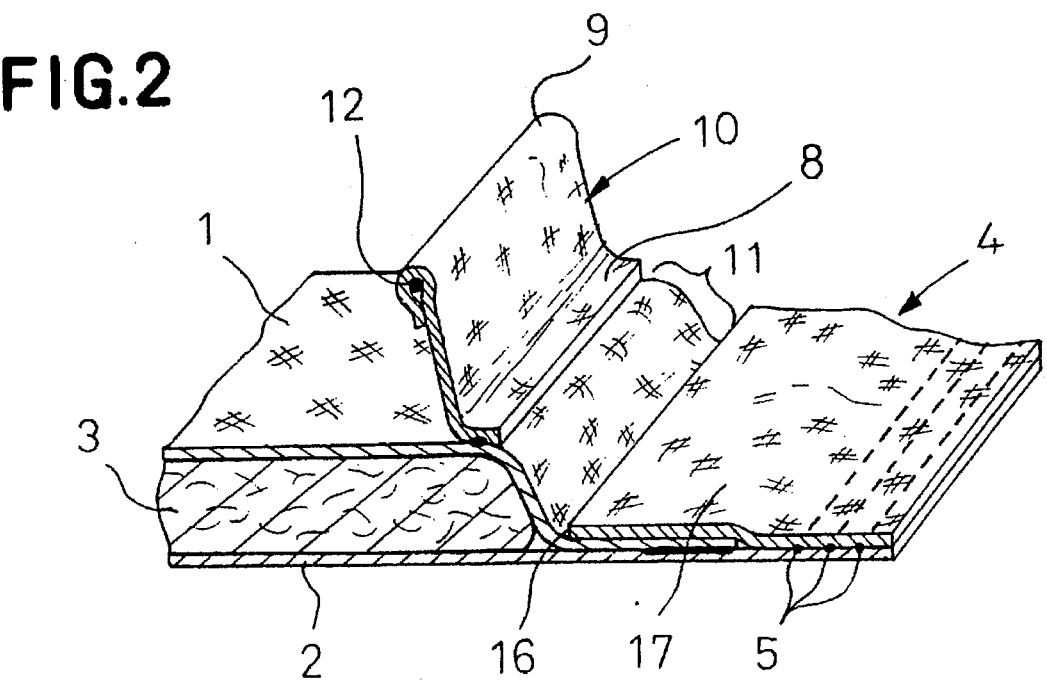
FIG. 2 is a fragmentary perspective sectional view taken along a line 2—2 in FIG. 1.

Referring to FIGS. 1 and 2, a diaper comprising a liquid-permeable topsheet 1, a liquid-impermeable backsheet 2, a liquid-absorbent core 3 sandwiched between the top- and backsheets 1, 2 and first side flaps 4 each being formed by portions of the top- and backsheets 1, 2 extending outwards from transversely opposite side edges of the liquid-absorbent core 3, and outer side zones of a cover sheet 15 as will be described in more detail. The topsheet 1 is dimensioned to be narrower than the backsheet so that transversely or laterally opposite side edges of the backsheet 2 extend beyond the corresponding side edges of the topsheet 1. The top- and backsheets 1, 2 are bonded together by means of adhesive, heat welding or ultrasonic welding at least along their peripheral zones overlapping each other. Between the portions of the backsheet 2 extending outwards beyond the side edges of the topsheet 1 and transversely opposite outer zones of the cover sheet 15 there are provided elastic members 5, respectively, serving to make the first side flaps 4 elastically stretchable longitudinally thereof. Portions of the top- and backsheets 1, 2 extending outward from longitudinally opposite ends of the liquid-absorbent core 3 together form end flaps 6 that contain, between these sheets elastic members 7, respectively, serving to make these end flaps 6 elastically stretchable transversely thereof.

The diaper further comprises second side flaps 10 each having a proximal edge 8 and a distal edge 9 to serve as a substantially moisture-permeable liquid-barrier. The second side flaps 10 have their proximal edges 8 bonded to the top surface of the topsheet 1 overlying the top surface of the liquid-absorbent core 3 by means of adhesive, heat welding, or ultrasonic welding so that the topsheet 1 is exposed along the laterally opposite side edge surfaces of the liquid-absorbent core 3. The zones of the topsheet 1 exposed in this manner along the laterally opposite side edge surfaces of the liquid-absorbent core 3 are designated by reference numeral 11 in FIG. 2. Folded edges defining the respective distal edges 9 contain an elastic member 12 to make these distal edges 9 elastically stretchable longitudinally thereof. The second side flaps 10 are collapsed inwards and bonded to the top surface of the topsheet 1 by means of adhesive, heat welding or ultrasonic welding at their longitudinally opposite ends as they are stretched longitudinally thereof so that they are normally biased to rise under their contraction.

The diaper further comprises the previously mentioned cover sheet 15 centrally provided with an opening 14 extending longitudinally thereof and substantially serving as a liquid-barrier. The cover sheet 15 is bonded at least along its outer peripheral zone to the top surface of the topsheet 1 and the longitudinally opposite ends 13 of the respective second side flaps 10 by means of adhesive, heat welding or ultrasonic welding. With the components bonded together in this manner, in addition to the exposed zones 11, intermediate zones of the respective second side flaps 10 except longitudinally opposite ends 13 as well as the intermediate zone defined between the second side flaps 10 are exposed, and transversely opposite side edges 16 of the opening 14 substantially coincide with the laterally opposite side edges of the liquid-absorbent core 3 at its bottom. The width of each exposed zone 11 is preferably dimensioned to be less than 5 mm in order to minimize soaking out of liquid excretions possibly taking place through this zone 11. When it is desired to dimension the height or thickness of the liquid-absorbent core 3 to be less than 5 mm, it is preferred to dimension the laterally opposite side edges at its bottom to be lower or thinner than its remaining portion. The use of the cover sheet 15 is advantageous in that the peripheral zone of the top (i.e., inner) surface of the diaper can serve as a liquid-barrier alleviating the diffusion of liquid excretions. Another feature of the invention, i.e., is that the liquid-impermeable backsheet 2 and the liquid-barrier cover sheet 15 are directly bonded together along the transversely opposite outer side zones with no portion of the topsheet 1 interposed therebetween. This is advantageous in that no soaking out of liquid excretions can occur between the backsheet 2 and the cover sheet 15.

When the second side flaps 10 vertically rise, the outermost edges of their distal edges 9 have preferably their height dimension above the top surface of the respective first side flaps 4 less than the width dimension of the respective first side flaps 4. It is also possible to collapse the longitudinally opposite ends 13 of the second side flaps 10 outwards, instead of collapsing inwards as in the embodiment described herein, before they are bonded to the top surface of the topsheet 1 without departure from the scope of the invention. However, the ends 13 are preferably collapsed inwards in order to assure that the distal edges 9 of the second side flaps 10 should not extend beyond the outer side edges of the respective first side flaps 4 even when the respective second side flaps 10 are forcibly collapsed by the wearer's thighs further outwards. The second side flaps 10 preferably have a flexibility higher than a flexibility of the first side flaps 4 and the elastic members 12 associated with the former preferably have a stretching stress lower than a stretching stress of the elastic members 5 associated with the latter. It is desirable that the second side flaps 10 are sufficiently flexible to protect the wearer's groin from pain and marks due to pressure, since the distal edges 9 of the second side flaps 10 are normally kept in contact with the wearer's groin.

Though not illustrated and as will be apparent without illustration, it is also possible that the cover sheet 15 is not used and sheets (referred to hereinafter as side sheets) corresponding to the respective side zones 17 cut off from said cover sheet 15 are bonded to the corresponding zones of the respective first side flaps 4. It should be understood that the inner side edges of these side sheets or the side edges 16 of the opening 14 may be bonded or not bonded to the top surface of the topsheet 1.

A rear waist section of the diaper is provided at transversely opposite ends with pressure-sensitive adhesive tape fasteners 18 adapted to be detachably fixed on the outer surface of a front waist section. It should be understood that the invention is applicable not only to a so-called open type diaper as has been described hereinabove but also to a so-called closed type or pant type diaper (not shown) having front and rear waist sections welded to each other at transversely opposite ends thereof.

To execute the invention, materials well known for such articles may be used. For example, the topsheet 1 may be formed by a nonwoven fabric made of hydrophobic fibers or a porous plastic film. The backsheet 2 may be formed by a plastic film which is liquid-impermeable but moisture-permeable. The liquid-absorbent core 3 may be formed by fluff pulp mixed with superabsorbent polymer powders, and the second side flaps 10 as well as the cover sheet 15 may be formed by a nonwoven fabric made of hydrophobic fibers (water-proofed, if necessary), while the elastic members 5, 7, 12 may be formed by natural or synthetic rubber and elastomer.

What is claimed is:

1. A disposable absorbent article having a liquid-permeable topsheet, a liquid-impermeable backsheet, a liquid-absorbent core sandwiched between said topsheet and said backsheet, first stretchable side flaps comprised of portions of said topsheet and said backsheet extending outwards from transversely opposite side edges of said liquid-absorbent core, second stretchable side flaps disposed along the respective side edges of said liquid absorbent core, said second side flaps each having a proximal edge, a distal edge and longitudinally opposite ends fixed in a collapsed state, wherein said second stretchable side flaps substantially function as liquid-barriers and have said proximal edges bonded to a top surface of said topsheet overlying a top surface of said liquid-absorbent core, and said first stretchable side flaps, outwardly adjacent said side edges, have top surfaces covered with side sheets functioning as liquid-barriers to prevent diffusion of liquid excretions from said liquid-absorbent core which is liquid-permeable along surfaces of said transverse opposite side edges of said core cover sheet centrally provided with an opening extending in a longitudinal direction thereof, said cover sheet covering an outer peripheral zone of the topsheet as well as the longitudinally opposite ends of the respective second stretchable side flaps, an outer peripheral zone of said cover sheet is bonded to said outer peripheral zone of the topsheet as well as to said longitudinally opposite ends of the respective second stretchable side flaps and wherein respective outer side zones of said cover sheet define said side sheets.

2. The article according to claim 1, wherein the portions of said topsheet extending outwards from the transversely opposite side edges of the liquid-absorbent core to constitute part of the respective first side flaps are narrower than the portions of said backsheet extending from said opposite side edges of said liquid-absorbent core so as to also constitute part of said first stretchable side flaps, and wherein outermost side edges of the respective side sheets extend from said laterally opposite side edges of the liquid-absorbent core and are bonded directly to the backsheet with no portion of the topsheet being interposed between the backsheet and the respective side sheets in outer zones of said first side flaps.

* * * * *